(12) United States Patent
Erhardt et al.

(10) Patent No.: US 9,919,303 B2
(45) Date of Patent: Mar. 20, 2018

(54) BRANCHED-CHAIN FATTY ACIDS AS LIQUID CATION EXCHANGERS

(71) Applicants: Frank Erhardt, Bielefeld (DE); Lukas Falke, Bielefeld (DE); Ralf Kelle, Guetersloh (DE); Harald Haeger, Luedinghausen (DE); Thomas Haas, Muenster (DE); Hans-Georg Hennemann, Bedburg (DE); Oliver Thum, Ratingen (DE); Martin Roos, Haltern am See (DE); Markus Poetter, Shanghai (CN)

(72) Inventors: Frank Erhardt, Bielefeld (DE); Lukas Falke, Bielefeld (DE); Ralf Kelle, Guetersloh (DE); Harald Haeger, Luedinghausen (DE); Thomas Haas, Muenster (DE); Hans-Georg Hennemann, Bedburg (DE); Oliver Thum, Ratingen (DE); Martin Roos, Haltern am See (DE); Markus Poetter, Shanghai (CN)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/419,580

(22) PCT Filed: Jul. 24, 2013

(86) PCT No.: PCT/EP2013/065563
§ 371 (c)(1),
(2) Date: Feb. 4, 2015

(87) PCT Pub. No.: WO2014/029577
PCT Pub. Date: Feb. 27, 2014

(65) Prior Publication Data
US 2015/0209775 A1    Jul. 30, 2015

(30) Foreign Application Priority Data
Aug. 21, 2012 (EP) .................................... 12181153

(51) Int. Cl.
| | | |
|---|---|---|
| *B01J 39/04* | (2017.01) | |
| *C07C 209/90* | (2006.01) | |
| *B01J 39/16* | (2017.01) | |
| *C02F 1/42* | (2006.01) | |
| *C02F 1/26* | (2006.01) | |
| *C07C 227/40* | (2006.01) | |
| *C07C 209/84* | (2006.01) | |
| *C02F 101/30* | (2006.01) | |
| *C02F 101/38* | (2006.01) | |
| *C02F 103/36* | (2006.01) | |

(52) U.S. Cl.
CPC ............... *B01J 39/04* (2013.01); *B01J 39/16* (2013.01); *C02F 1/26* (2013.01); *C02F 1/42* (2013.01); *C07C 209/90* (2013.01); *C02F 2001/425* (2013.01); *C02F 2101/30* (2013.01); *C02F 2101/38* (2013.01); *C02F 2103/36* (2013.01); *C07C 209/84* (2013.01); *C07C 227/40* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 4,334,095 A | 6/1982 | Baniel | |
| 4,990,626 A * | 2/1991 | Hutchinson | .......... C07D 209/48 548/462 |
| 6,171,501 B1 | 1/2001 | Eyal et al. | |
| 6,509,439 B1 * | 1/2003 | Hayes | .................... C08G 69/28 528/310 |
| 6,620,970 B2 | 9/2003 | Schiffer et al. | |
| 6,639,108 B2 | 10/2003 | Schiffer et al. | |
| 6,764,671 B2 | 7/2004 | Haas et al. | |
| 6,861,540 B2 | 3/2005 | Herwig et al. | |
| 6,878,836 B2 | 4/2005 | Haas et al. | |
| 7,005,528 B2 | 2/2006 | Haas et al. | |
| 7,030,052 B2 | 4/2006 | Stochniol et al. | |

(Continued)

FOREIGN PATENT DOCUMENTS

| | | |
|---|---|---|
| EP | 0 049 429 A1 | 4/1982 |
| EP | 2 489 432 | 8/2012 |

(Continued)

OTHER PUBLICATIONS

U.S. Appl. No. 14/380,483, filed Aug. 22, 2014, Schiemann, et al.
U.S. Appl. No. 14/367,610, filed Jun. 20, 2014, Haas, et al.
U.S. Appl. No. 14/435,339, filed Apr. 13, 2015, Engel, et al.
U.S. Appl. No. 14/649,414, filed Jun. 3, 2015, Schaffer et al.
U.S. Appl. No. 14/763,378, filed Jul. 24, 2015, Haas, et al.
International Search Report dated Aug. 14, 2013 in PCT/EP2013/065563 Filed Jul. 24, 2013.

(Continued)

*Primary Examiner* — Clinton Brooks
(74) *Attorney, Agent, or Firm* — Oblon, McClelland, Maier & Neustadt, L.L.P.

(57) ABSTRACT

The present invention relates to a method for removing an organic compound from an aqueous solution, comprising the steps of providing the aqueous solution which contains the organic compound, and a hydrophobic organic solution, where the latter comprises a liquid hydrophobic cation exchanger, contacting the aqueous solution and the hydrophobic organic solution, and separating off the hydrophobic organic solution from the aqueous solution, wherein the liquid hydrophobic cation exchanger is a saturated alkanoic acid having at least one alkyl substituent, where the organic compound is an organic compound having at least one positive charge and a neutral or positive total charge.

10 Claims, No Drawings

(56) References Cited

U.S. PATENT DOCUMENTS

| | | |
|---|---|---|
| 7,049,450 B2 | 5/2006 | Hofen et al. |
| 7,091,384 B2 | 8/2006 | Jaeger et al. |
| 7,507,862 B2 | 3/2009 | Stochniol et al. |
| 7,718,268 B2 * | 5/2010 | Guth .................. D06M 11/155 252/8.63 |
| 7,879,938 B2 | 2/2011 | Häger et al. |
| 8,399,658 B2 | 3/2013 | Hengstermann et al. |
| 8,404,470 B2 | 3/2013 | Thum et al. |
| 8,445,720 B2 | 5/2013 | Hannen et al. |
| 8,703,451 B2 | 4/2014 | Haas et al. |
| 8,703,993 B2 | 4/2014 | Hannen et al. |
| 8,809,576 B2 | 8/2014 | Schraven et al. |
| 8,835,691 B2 | 9/2014 | Klasovsky et al. |
| 8,927,773 B2 | 1/2015 | Klasovsky et al. |
| 8,946,463 B2 | 2/2015 | Klasovsky et al. |
| 8,981,159 B2 | 3/2015 | Klasovsky et al. |
| 8,999,684 B2 | 4/2015 | Poetter et al. |
| 9,000,223 B2 | 4/2015 | Micoine et al. |
| 9,012,227 B2 | 4/2015 | Karau et al. |
| 9,315,443 B2 * | 4/2016 | Erhardt .................. C07C 67/62 |
| 2002/0087036 A1 | 7/2002 | Haas et al. |
| 2003/0212298 A1 | 11/2003 | Brasse et al. |
| 2010/0266518 A1 | 10/2010 | Springer et al. |
| 2010/0291644 A1 | 11/2010 | Marx et al. |
| 2011/0118433 A1 | 5/2011 | Pötter et al. |
| 2011/0251399 A1 | 10/2011 | Dingerdissen et al. |
| 2012/0034665 A1 | 2/2012 | Haas et al. |
| 2012/0315366 A1 | 12/2012 | Zehnacker et al. |
| 2013/0052700 A1 | 2/2013 | Poetter et al. |
| 2013/0164797 A1 | 6/2013 | Gielen et al. |
| 2013/0165685 A1 | 6/2013 | Hannen et al. |
| 2014/0039071 A1 | 2/2014 | Thum et al. |
| 2014/0039210 A1 | 2/2014 | Erhardt et al. |
| 2014/0054224 A1 | 2/2014 | Erhardt et al. |
| 2014/0120587 A1 | 5/2014 | Haas et al. |
| 2014/0141478 A1 | 5/2014 | Schaffer et al. |
| 2014/0178948 A1 | 6/2014 | Schaffer et al. |
| 2014/0186905 A1 | 7/2014 | Schaffer et al. |
| 2014/0242646 A1 | 8/2014 | Pötter et al. |
| 2014/0256904 A1 | 9/2014 | Schaffer et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |
| 2015/0111253 A1 | 4/2015 | Schaffer et al. |
| 2015/0209775 A1 | 7/2015 | Erhardt et al. |

FOREIGN PATENT DOCUMENTS

| | | | |
|---|---|---|---|
| JP | 59-20252 A | 2/1984 | |
| JP | 62-164633 A | 7/1987 | |
| JP | 2011-505854 A | 3/2011 | |
| JP | 2012-106935 A | 6/2012 | |
| WO | WO9802411 * | 7/1997 | ........... C07C 227/40 |
| WO | WO 98/02411 A1 | 1/1998 | |
| WO | WO 02/36260 A1 | 5/2002 | |
| WO | WO 03/051544 A1 | 6/2003 | |
| WO | WO 2004/048355 A1 | 6/2004 | |
| WO | WO 2005/000827 A1 | 1/2005 | |
| WO | WO 2011/036000 A1 | 3/2011 | |
| WO | WO 2012/110125 A1 | 8/2012 | |
| WO | WO2012110124 * | 8/2012 | ........... C07C 227/40 |
| WO | WO 2013/083412 A1 | 6/2013 | |
| WO | WO 2013/092426 A1 | 6/2013 | |
| WO | WO 2013/092547 A1 | 6/2013 | |
| WO | WO 2013/110557 A1 | 8/2013 | |
| WO | WO 2013/124401 A1 | 8/2013 | |
| WO | WO 2013/135650 A1 | 9/2013 | |
| WO | WO 2014/029577 A1 | 2/2014 | |
| WO | WO 2014/079683 A1 | 5/2014 | |
| WO | WO 2014/095986 A1 | 6/2014 | |

OTHER PUBLICATIONS

Patricia D. Mackenzie, et al., "Combined solvent extraction and stripping for removal and isolation of ammonia from sour waters", Industrial & Engineering Chemistry Process Design and Development, vol. 24, No. 4, XP055054507, Oct. 1985, pp. 1192-1200.

* cited by examiner

BRANCHED-CHAIN FATTY ACIDS AS LIQUID CATION EXCHANGERS

The present invention relates to a method for removing an organic compound from an aqueous solution, comprising the steps providing the aqueous solution which contains the organic compound and a hydrophobic organic solution, wherein the latter comprises a liquid hydrophobic cation exchanger, contacting the aqueous solution and the hydrophobic organic solution, and separating off the hydrophobic organic solution from the aqueous solution, wherein the liquid hydrophobic cation exchanger is a saturated alkanoic acid having at least one alkyl substituent, wherein the organic compound is an organic compound having at least one positive charge and a neutral or positive total charge.

A fundamental problem in the biotechnological production of fine chemicals proceeding from renewable raw materials, which fine chemicals would otherwise be synthesised proceeding from fossil fuels, is transferring the product once obtained, which is typically present in a large-volume aqueous phase, to an organic phase. This transfer is carried out, firstly, in order to concentrate a finished intermediate or end product and optionally permit the synthetic processing in the following reaction steps in an organic solution, and secondly in order to improve the yield of the reaction in the aqueous phase by removing the desired product, or to permit the reaction to take place at all in a technically logical context. Direct thermal concentration from the large-volume aqueous solution of the product which is frequently present at low concentrations is generally not expedient.

The distribution of a compound in a two-phase system in equilibrium comprising an aqueous hydrophilic phase and an organic hydrophobic phase which do not mix depends critically on the physicochemical properties of the respective compound. Whereas compounds having a high fraction of, or exclusively consisting of, unsubstituted hydrocarbons predominantly accumulate in the hydrophobic phase, compounds having a high fraction of polar groups, such as heteroatom-containing functionalities, and very particularly, compounds with charges predominantly, or virtually exclusively, are situated in the aqueous phase, which makes transfer to an organic phase more difficult.

The distribution of a compound in the said two-phase system, after equilibrium is established, is frequently described using distribution coefficients, for example in accordance with the Nernst equation $$\alpha = c_{phase\ 1}/c_{phase\ 2},$$

A special distribution coefficient is $K_{ow}$, also termed P value, which characterizes the distribution equilibrium of a compound between an octanol phase and an aqueous phase:

$$K_{ow} = P = c_{octanol}/c_{water}$$

Examples of an organic compound that is in high demand industrially and is positively charged in aqueous solution at physiological pH are 12-aminolauric acid (ALA) and derivatives thereof, in particular the methyl ester (ALAME). ALA is an important feedstock in the production of polymers. Usually, ALA is produced proceeding from fossil raw materials in a process having a low yield via laurolactam which is synthesised by trimerisation of butadiene, subsequent hydrogenation with formation of cyclododecane, subsequent oxidation to cyclododecanone, reaction with hydroxylamine and subsequent Beckmann rearrangement. A highly promising pathway for the biotechnological production of ALA, or ALAME, is described in DE10200710060705.

The prior art teaches obtaining positively-charged organic compounds by contacting an aqueous reaction mixture comprising a metabolically active cell with an organic phase comprising an organic solvent. For instance, DE10200710060705, for example, describes obtaining the product ALAME from an organic reaction mixture by shaking with ethyl acetate. Asano et al. (2008) disclose the extraction of ALA with toluene from an aqueous reaction solution comprising an ALA-synthesising enzyme (Asano, Y., Fukuta, Y., Yoshida, Y., and Komeda, H. (2008): The Screening, Characterisation, and Use of ω-Laurolactam Hydrolase: A New Enzymatic Synthesis of 12-Aminolauric Acid, *Biosc. Biotechn. Biochem.*, 72 (8), 2141-2150).

The object, therefore, of the present invention is to develop a method for removing positively-charged organic compounds, particularly ω-aminocarboxylic acids, having at least one positive charge from an aqueous reaction mixture, wherein a position of the distribution equilibrium as advantageous as possible between reaction mixture and a hydrophobic organic phase used as extraction medium is desired, i.e. the distribution equilibrium shall lie as far as possible on the side of the hydrophobic organic phase.

A further object of the invention is to develop a method for removing organic compounds having at least one positive charge, particularly ω-aminocarboxylic acids, from an aqueous solution comprising a metabolically active cell, using a hydrophobic organic phase as extraction medium, wherein the distribution equilibrium lies as far possible on the side of the hydrophobic organic phase.

A further object of the invention is to develop a method for removing organic compounds having at least one positive charge, particularly ω-aminocarboxylic acids, from an aqueous solution, using a hydrophobic organic solution as extraction medium, which impairs or retards as little as possible the growth of biotechnologically relevant microorganisms, in particular *Escherichia coli*, and/or decreases as little as possible the count of cells that are capable of cell division and/or of viable and/or respiratorily and/or metabolically active and synthetically active cells in the course of this.

A further object of the invention is to develop a method for removing organic compounds having at least one positive charge, particularly ω-aminocarboxylic acids, from an aqueous solution, using a hydrophobic organic solution as extraction medium, in which the keeping quality and/or the recoverability, particularly with respect to constant content of liquid hydrophobic cation exchanger or purity of the cation exchanger after recovery, of the hydrophobic organic solution is as good as possible.

Finally, the object of the invention is to discover a method for removing an organic compound having at least one positive charge, particularly ω-aminocarboxylic acids, from an aqueous solution comprising a metabolically active cell, using a hydrophobic organic phase as extraction medium, in which the totality of the properties critical for the yield, the total conversion rate and rapid operability of an underlying biotechnological synthetic method, in particular the toxicity of the organic phase towards a metabolically active cell, and the uptake of the compound into the organic extraction medium, is optimised with respect to the overall yield or a more rapid sequence or, in the case of a continuous process, a usability of the metabolically active cell for as long as possible, particularly in the event that the organic compound having at least one positive charge is the product or an intermediate of the synthetic method which is synthesised with participation of a catalytic activity of the metabolically active cell.

These and other objects are achieved by the subject matter of the present application and particularly also by the subject matter of the accompanying independent claims, with embodiments arising from the dependent claims.

In a first aspect, the problem underlying the invention is solved by a method for removing an organic compound from an aqueous solution, comprising the steps
a) providing the aqueous solution which contains the organic compound, and a hydrophobic organic solution, wherein the latter comprises a liquid hydrophobic cation exchanger,
b) contacting the aqueous solution and the hydrophobic organic solution, and
c) separating off the hydrophobic organic solution from the aqueous solution,
wherein the liquid hydrophobic cation exchanger is a saturated alkanoic acid having at least one alkyl substituent,
wherein the organic compound is an organic compound having at least one positive charge and a neutral or positive total charge.

In a first embodiment of the first aspect, the problem is solved by a method wherein the organic compound is a compound of the formula $$NR^2R^3H^+\text{-A-COOR}^1 \quad (I)$$

or $$NR^2R^3H^+\text{-A-}NR^4R^5H^+ \quad (II),$$

wherein $R^1$ is hydrogen, methyl, ethyl, propyl, isopropyl or a negative charge,
wherein A is an alkylene group having at least three, preferably at least six, particularly preferably eight, carbon atoms, which is preferably unsubstituted and straight-chain,
and wherein $R^2$, $R^3$, $R^4$, and $R^5$, in each case and independently of one another, are selected from the group consisting of hydrogen, methyl, ethyl and propyl.

In a second embodiment of the first aspect, which is also an embodiment of the first embodiment, the problem is solved by a method wherein the pH in the aqueous solution in step b) is 6 to 8, preferably 6.2 to 7.2.

In a third embodiment of the first aspect, which is also an embodiment of the first to second embodiments, the problem is solved by a method wherein the amount-of-substance ratio of liquid cation exchanger to organic compound in step b) is at least 1.

In a fourth embodiment of the first aspect, which is also an embodiment of the first to third embodiments, the problem is solved by a method wherein the volumetric ratio of organic solution to aqueous solution is 1:10 to 10:1.

In a fifth embodiment of the first aspect, which is also an embodiment of the first to fourth embodiments, the problem is solved by a method wherein the liquid cation exchanger is a branched-chain fatty acid of the formula $(H_3C)_2CH\text{—}(CH_2)_n\text{—COOH}$ or an unprotonated form thereof and n is at least 4, preferably at least 8, and most preferably is 14.

In a sixth embodiment of the first aspect, which is also an embodiment of the first to fifth embodiments, the problem is solved by a method wherein the liquid cation exchanger is a saturated alkanoic acid having at least one alkyl substituent which preferably comprises in total at least 12 carbon atoms.

In a seventh embodiment of the first aspect, which is also an embodiment of the first to sixth embodiments, the problem is solved by a method wherein the aqueous solution additionally comprises a metabolically active cell.

In an eighth embodiment of the first aspect, which is also an embodiment of the first to seventh embodiments, the problem is solved by a method wherein the organic compound is a compound toxic to a cell, preferably a bacterial cell.

In a ninth embodiment of the first aspect, which is also an embodiment of the first to eighth embodiments, the problem is solved by a method wherein the organic solution additionally contains at least one organic solvent, preferably a fatty acid and/or a fatty acid ester.

In a tenth embodiment of the first aspect, which is also an embodiment of the first to ninth embodiments, the problem is solved by a method wherein the hydrophobic organic solution contains the liquid hydrophobic cation exchanger in a volumetric fraction of 20 to 80%, preferably 25 to 75%.

In an eleventh embodiment of the second aspect, which is also an embodiment of the first to tenth embodiments of the first aspect, the organic compound is a diamine selected from the group consisting of 1,4-butanediamine, 1,5-pentanediamine, 1,6-hexanediamine, 1,8-octanediamine, 1,14-tetradecanediamine, 1,18-octadecanediamine, 2-methyl-1,5-diaminopentane, 2,2-dimethyl-1,5-diaminopentane, 4,4'-diaminodicyclohexylmethane, 3,3'-dimethyl-4,4'-diaminodicyclohexylmethane, 3,3',5,5'-tetramethyl-4,4'-diaminodicyclohexylmethane, m- or p-xylylenediamine, 2,2,4- or 2,4,4-trimethylhexamethylenediamine, 1,4-diaminocyclohexane, 4,4'-diaminodicyclohexylpropane, isophoronediamine, meta-xylylenediamine and para-xylylenediamine.

In a twelfth embodiment of the second aspect, which is also an embodiment of the first to eleventh embodiments, the temperature in step b) is between 28 and 70° C., preferably between 30 and 37° C.

In a second aspect, the problem underlying the invention is solved by a reaction mixture comprising an aqueous solution which contains an organic compound and a hydrophobic organic solution,
wherein the hydrophobic organic solution comprises a liquid hydrophobic cation exchanger,
wherein the liquid hydrophobic cation exchanger is a saturated alkanoic acid having at least one alkyl substituent,
and wherein the organic compound is an organic compound having at least one positive charge and a neutral or positive total charge.

In a first embodiment of the second aspect, the problem is solved by a reaction mixture wherein the organic compound is a compound of the formula $$NR^2R^3H^+\text{-A-COOR}^1 \quad (I)$$

or $$NR^2R^3H^+\text{-A-}NR^4R^5H^+ \quad (II),$$

wherein $R^1$ is hydrogen, methyl, ethyl, propyl, isopropyl or a negative charge,
wherein A is an alkylene group having at least three, preferably at least six, particularly preferably eight, carbon atoms which is preferably unsubstituted and straight-chain,
and wherein $R^2$, $R^3$, $R^4$, and $R^5$ in each case and independently of one another, are selected from the group consisting of hydrogen, methyl, ethyl and propyl.

In a second embodiment of the second aspect, which is also an embodiment of the first embodiment of the first aspect, the problem is solved by a reaction mixture wherein the liquid hydrophobic cation exchanger is a branched-chain fatty acid of the formula $(H_3C)_2CH\text{—}(CH_2)_n\text{—COOH}$ or an unprotonated form thereof and n is at least 4, preferably at least 8, and most preferably 14.

In a third embodiment of the second aspect, which is also an embodiment of the first to second embodiments of the first aspect, the liquid cation exchanger is a saturated alkanoic acid having at least one alkyl substituent which preferably comprises in total at least 12 carbon atoms.

In a fourth embodiment of the second aspect, which is also an embodiment of the first to third embodiments of the first aspect, the aqueous solution additionally comprises a metabolically active cell.

In a fifth embodiment of the second aspect, which is also an embodiment of the first to fourth embodiments of the second aspect, the organic compound is a diamine selected from the group consisting of 1,4-butanediamine, 1,5-pentanediamine, 1,6-hexanediamine, 1,8-octanediamine, 1,14-tetradecanediamine, 1,18-octadecanediamine, 2-methyl-1,5-diaminopentane, 2,2-dimethyl-1,5-diaminopentane, 4,4'-diaminodicyclohexylmethane, 3,3'-dimethyl-4,4'-diaminodicyclohexylmethane, 3,3',5,5'-tetramethyl-4,4'-diaminodicyclohexylmethane, m- or p-xylylenediamine, 2,2,4- or 2,4,4-trimethylhexamethylenediamine, 1,4-diaminocyclohexane, 4,4'-diaminodicyclohexylpropane, isophoronediamine, meta-xylylenediamine and para-xylylenediamine.

Further embodiments of the second aspect comprise all embodiments of the first aspect of the present invention.

The inventors of the present invention have found that the efficiency of the removal of an organic compound having a positive charge from an aqueous solution into a hydrophobic organic solution can surprisingly be increased if this organic solution comprises a liquid cation exchanger which is a saturated alkanoic acid having at least one alkyl substituent. Without wishing to be bound to any theory, the inventors of the present invention presume that the negative charge or the negative charges of the liquid cation exchanger interacts interact ionically with the one positive charge or the multiplicity of positive charges of the organic compounds and that this interaction leads to a masking of at least one positive charge, which increases the solubility in the organic phase.

The present invention provides the use of a saturated alkanoic acid having at least one alkyl substituent as a liquid hydrophobic cation exchanger for removing an organic compound having a positive charge from an aqueous solution, preferably with accumulation of the organic compound in the hydrophobic organic solution. In a preferred embodiment, the expression "saturated alkanoic acid having at least one alkyl substituent" is taken to mean an alkanoic acid of the formula $CH_3$—$(CH_2)_n$—COOH or an unprotonated form thereof, in which at least one hydrogen atom from the alkyl chain is exchanged for an alkyl substituent of the formula $(CH_2)_m$—H, wherein n and m in each case and independently of one another can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In a most preferred embodiment, the saturated alkanoic acid having at least one alkyl substituent is a compound from the group consisting of isostearic acid, isopalmitic acid, isomyristic acid, phytanic acid, 2 hexyldecanoic acid, 2-butyloctanoic acid, 15-methylhexadecanoic acid, 13-methyltetradecanoic acid. In a particularly preferred embodiment, the last carbon atom but one is substituted in the alkyl chain, particularly preferably with a methyl group. Mixtures that are useable according to the invention are explicitly mixtures of various saturated alkanoic acids having at least one alkyl substituent, optionally with further liquid hydrophobic cation exchangers that are structurally different from the latter.

In a preferred embodiment, the liquid cation exchanger is a branched-chain fatty acid which exclusively comprises substituents that are other than cyclic substituents, i.e. the molecule is linear, therefore does not comprise any ring-type structures.

As with all compounds in this application, a saturated alkanoic acid having at least one alkyl substituent, in a preferred embodiment, equally comprises unprotonated, partially and completely protonated forms of the compound.

The teaching according to the invention is suitable for the removal of structurally diverse organic compounds having a positive charge and positive or neutral total charge from an aqueous solution. In a preferred embodiment, the organic compound is a compound of the formula

$$NR^2R^3H^+\text{-}A\text{-}COOR^1 \qquad (I)$$

or

$$NR^2R^3H^+\text{-}A\text{-}NR^4R^5H^+ \qquad (II),$$

wherein $R^1$ is hydrogen, methyl, ethyl, propyl, isopropyl or a negative charge, wherein A is an alkylene group having at least three, preferably at least six, particularly preferably eight, carbon atoms which is preferably unsubstituted and straight-chain. A can be a branched or unbranched, linear or cyclic alkane or an aromatic or heteroaromatic which is substituted with at least the two substituents given in formula (II). In a particularly preferred embodiment, the organic compound is a compound of the formula II and A is an alkylene chain of the formula —$(CH2)n$-, wherein n is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40, and particularly preferably, additionally 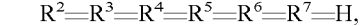 $R^2=R^3=R^4=R^5=R^6=R^7=H$, and wherein $R^2$, $R^3$, $R^4$, and $R^5$, in each case and independently of one another, are selected from the group consisting of hydrogen, methyl, ethyl and propyl. In a preferred embodiment it is aminolauric acid or an ester thereof, preferably the methyl ester.

In a preferred embodiment, the expression "liquid cation exchanger", as used herein, means a compound soluble in a hydrophobic organic solvent that is liquid at room temperature, which compound, owing to a negative charge located at least in part on the carboxylate group of the alkanoic acid, is capable of developing at least transiently an ionic interaction with at least one cation.

The aqueous solution from which the organic compound is removed is preferably a water-containing buffer solution or an aqueous culture medium which still more preferably contains water as predominant solvent. For example, the solvent fraction of the water in the aqueous solution is more than 10, 20, 30, 40, 50, 60, 70, 80, 90, 95, 99 percent by volume or 100 percent by volume. Those skilled in the art know numerous aqueous buffer culture media which are suitable for maintaining or culturing cells, in particular cells of biotechnological importance. These include, equally, complete media such as LB media, minimal media such as M9 media, minimal media having complex components such as yeast extract or peptone, combinations of the above-mentioned and also selective media, for example those which have a high salt concentration and therefore only permit the growth of halophilic or at least halotolerant organisms. In a preferred embodiment, the expression "aqueous culture medium", as used herein, is taken to mean a water-based reaction medium which, with respect to all relevant factors, in particular pH, salt content and temperature, is of such a nature that it maintains or promotes the viability of cells present therein, preferably microorganisms, and both aqueous culture medium and hydrophobic organic phase are present in the liquid form. The temperature requirements of various biotechnologically important cells can be found in microbiology and molecular biology textbooks, e.g. Fuchs/Schlegel (2007) Allgemeine Mikrobiologie [General Microbiology], 2008, Georg Thieme Verlag. In a preferred embodiment, the pH of the aqueous culture medium at the time point of contacting is between 4 and 9, more preferably between 4.5 and 8.5, most preferably between 6.2 and 7.2. In a preferred embodiment, the pH of the aqueous culture medium in step b) is kept in the range from pH 4 to 9, more preferably between 4.5 and 8.5, most preferably between 6.2 and 7.2 for at least 0.5 h, more preferably at least 2 h, still more preferably at least 6 h, most preferably at least 12 h. Those skilled in the art know from the art how the pH of an aqueous solution, in particular also an aqueous solution comprising metabolically active cells and media required for the culture thereof, can be adjusted and controlled by adding acid or base, for example sulphuric acid or ammonia water. In a further preferred embodiment, the temperature is between 0 and 45° C., more preferably between 15 and 40° C., most preferably between 20 and 37° C.

In a preferred embodiment of the present invention, the expression "contacting", as used herein, is taken to mean that two phases are exposed to one another directly, and in particular without intermediate connection of a physical barrier such as a membrane. The contacting in the simplest case is carried out by placing the two phases into the same vessel and mixing them with one another in a suitable manner, for example by stirring. Quite explicitly, for the implementation of the teaching according to the invention, it is possible, but in no way necessary, that a biphasic system is present. Rather, good mixing as continuous as possible of the total of the aqueous solution and the hydrophobic organic solution, for example by stirring, is instrumental to the removal of the organic solution from the aqueous solution.

In a preferred embodiment, the expression "has a charge", as used herein, means that a compound thus characterized has a corresponding charge on a suitable functional group, for example a positive charge on an ammonium group, in aqueous solution at pH 0 to 14, more preferably 2 to 12, 2 to 6, 8 to 12, 3 to 10, 6 to 8, most preferably at pH 7. In a preferred embodiment, it is a charge that is permanently present. In a further preferred embodiment, the expression "has a charge", as used herein, means that the corresponding functional group or compound is predominantly present with the corresponding charge at pH 7, i.e. at at least 50, more preferably 90, still more preferably 99%. For example, the molecule ethanolamine has a charge at pH 0. In this case, it is the protonated ammonium group. In a preferred embodiment, the expression "total charge" of a compound, in contrast, means the sum of all charges on the compound at pH 0 to 14, more preferably 2 to 12, 2 to 6, 8 to 12, 3 to 10, 6 to 8, most preferably at pH 7. For example, the compound glycine in aqueous solution at pH 6 has two charges, namely a negative charge on the carboxy function and a positive charge on the protonated amino group, i.e. in total a neutral total charge.

In a preferred embodiment of the invention, the expression "containing" is taken to mean the sense of "comprising", i.e. not exhaustive. In this context, a mixture containing A can, in addition to A, have other components. The wording "one or more charges" means at least one charge of the corresponding nature.

In a preferred embodiment, the expression "hydrophobic", as used herein, is taken to mean the ability of a liquid, in the presence of an aqueous phase and in equilibrium, i.e. in particular in the absence of counteracting measures such as stirring, to form a separate liquid phase clearly delimited from the aqueous phase. The liquid phase can be a coherent liquid phase or an emulsion. In a further preferred embodiment, the expression "hydrophobic", as used herein, is taken to mean the property of a compound to be substantially water-insoluble. Finally, the expression, in a further preferred embodiment, as used herein, is taken to mean that a compound designated in this manner has a P value (J. Sangster, *Octanol-Water Partition Coefficients: Fundamentals and Physical Chemistry*, Vol. 2 of *Wiley Series in Solution Chemistry*, John Wiley & Sons, Chichester, 1997), the logarithm to base 10 of which is greater than 0, more preferably greater than 0.5, still more preferably greater than 1, and most preferably greater than 2. Preferred organic solvents comprise, but are not restricted to, solvents from the group consisting of substituted and unsubstituted alkanes, cycloalkanes, cycloalkenes, aryls, fatty acids, fatty acid esters, alcohols, heterocycloalkanes, heterocycloalkenes and heteroaryls that are liquid at room temperature. The hydrophobic organic solution can also be a mixture comprising more than one hydrophobic organic solvent.

In a further embodiment of the present invention, the liquid ion exchanger is not toxic or is only moderately toxic with respect to metabolically active cells, particularly biotechnologically relevant microorganisms. The expression "toxic", as used herein, in a preferred embodiment of the invention, is taken to mean the property of a compound, on contact with the corresponding microorganisms, to decrease the growth rate thereof, to reduce the metabolic activity thereof, to increase the energy consumption thereof, to lower the optical density thereof or count of cells capable of growth, to reduce or inhibit the biotechnological metabolic activity or productivity thereof, and/or to lead directly to the death and lysis thereof. In a preferred embodiment, at least one of these actions is achieved in the case of a toxic compound even at a low concentration, preferably at a concentration of 1000, more preferably 100, still more preferably 50 or 25, most preferably 5 mg/l. Those skilled in the art know numerous methods useable as a matter of routine, by means of which the toxicity can be studied. These include, for example, measurement of the respiration of corresponding microorganisms via $O_2$ electrodes or off-gas analysis or comparative plating out of microorganism samples and subsequent counting of the colony forming units (cfus). In a preferred embodiment, a "moderate toxic activity" is taken to mean that microorganisms situated in a growth phase, in the presence of the compound, grow further and/or are metabolically active, but to a lower extent than a control which is incubated under identical conditions in the absence of the corresponding compound, and/or of a prolonged lag phase.

Aqueous and organic solutions are contacted under suitable conditions, and in particular over a time period which is sufficient for sufficient passage of the organic compound from the aqueous phase into the organic phase, ideally even for establishing the corresponding equilibrium. This time period and conditions can be determined by those skilled in the art in the context of routine experimentation. In a preferred embodiment, step b) lasts at least 0.25, 0.5, 1, 2, 3, 4, 5, 6, 7, 8, 9, 10, 12, 18, 24, 36 or 48 hours, or longer than such a time period. Additional information on possible ways for carrying out the invention are described in EP11154707.

The temperature in step b) depends not only on the properties of the liquid cation exchanger, but, in particular in the event that contacting the aqueous and organic solutions takes place when the reaction is proceeding in the aqueous phase, also on the temperature requirements of any reactions taking place in the aqueous phase. In particular in the event that a metabolically active cell is catalytically active in the aqueous phase, the temperature must be suitable for maintaining this activity. In a preferred embodiment, the temperature in step b) is 0 to 100° C., more preferably 20 to 80° C., 28 to 70° C., 30 to 37° C., 35 to 40° C.

The pH during step b) must also take into account the requirements of any reactions proceeding at the same time, of the mass transfer of the dissolved organic compound into the phase of the liquid ion exchanger, and of the stability of reactants, products, intermediates or agents. In a preferred embodiment, the pH is 3 to 8, more preferably 6 to 8, still more preferably 6.2 to 7.2. It may be necessary to keep the pH in the aqueous solution constant and/or control it in other ways by open-loop or closed-loop methods and thereby feed correction auxiliaries (e.g. ammonia water/ammonia gas, sulphuric acid, or the like).

In order to transfer the organic compound from the aqueous phase as completely as possible into the organic phase, a sufficient amount of the liquid hydrophobic cation exchanger is necessary. In a preferred embodiment of the present invention, the amount-of-substance ratio of liquid cation exchanger and organic compound in at least one step, in the case of a continuous process, totalled over the entire sequence of the reaction, is at least 1, i.e. per molecule of the organic compound, at least one molecule of liquid hydrophobic cation exchanger is used. In a still more preferred embodiment, the ratio is greater than 2, 3, 5, 10, 15 or 20, preferably 1.5 to 3.

The volumetric ratio of the organic solution to the aqueous solution is, together with the amount-of-substance ratio of cation exchanger/organic compound, of importance for an efficient method. In a particular embodiment, it is 100:1 to 1:100, more preferably 20:1 to 1:20, still more preferably 10:1 to 1:10, 4:1 to 1:4, 3:1 to 1:3, or most preferably 1:2 to 2:1.

In addition to the liquid hydrophobic cation exchanger, the hydrophobic organic phase can further contain a hydrophobic solvent. This can be used for increasing the absorption capacity of a liquid hydrophobic cation exchanger in the hydrophobic phase and preventing unwanted behaviour, for example flocculation. In a preferred embodiment, the solvent is a reagent of a reaction proceeding in the aqueous solution, most preferably the substrate of an enzyme-catalysed reaction proceeding in the aqueous solution. In a preferred embodiment, it is a fatty acid ester. In a particularly preferred embodiment, the solvent is a fatty acid ester, preferably methyl ester, of a fatty acid which acts as liquid hydrophobic cation exchanger. Mixtures of more than one solvent and one or more than one liquid hydrophobic cation exchanger can also be used as hydrophobic organic solution.

The fraction of the solvent, where present, of the hydrophobic organic phase, in a preferred embodiment, is 1 to 99 percent by volume (vol. %). In a preferred embodiment, the fraction of the solvent is 10 to 90, still more preferably 20 to 80, most preferably 25 to 75 vol.-%.

In a preferred embodiment, the metabolically active cell is a recombinant cell which is equipped with enzymes for producing the compound of the formula (I) or (II) and overexpresses at least one thereof, preferably all. Suitable enzymes which can be used for producing organic compounds of the formula (I) or (II), in particular alkanehydroxylases, AlkL, transaminases, aldehyde dehydrogenases and alanine dehydrogenases are described in the prior art, for example in DE10200710060705, EP11004029 or in PCT/EP2011/053834. In a preferred embodiment, the expression "metabolically active cell", as used herein, is taken to mean a living cell having metabolic activity, preferably a cell which expresses, or still more preferably, overexpresses, in active form, an enzyme relevant to the biotechnological production of the product of interest. The cell can be a prokaryote, including archaea, or a eukaryote, and in the case of a prokaryote, preferably from the group of genera comprising *Pseudomonas, Corynebacterium* and *Escherichia*. In a still more preferred embodiment, the cell is a bacterial cell, still more preferably a gram-negative bacterial cell, most preferably *E. coli*. In a further preferred embodiment, it is a eukaryotic cell, more preferably a fungal cell, still more preferably a yeast cell, most preferably *Saccharomyces* or *Candida, Pichia*, in particular *Candida tropicalis*. In a preferred embodiment, the expression "lower eukaryote", as used herein, means a eukaryote that is unicellular in all the phases of its existence, in contrast to higher eukaryotes which pass the predominant part of their life in the form of a multicellular organism having tissues comprising differentiated cells. The expression "cell", in a particular embodiment, is used synonymously and exchangeably with the expression "microorganism" in this application. In addition, the cell can be an isolated cell or a mixture of various cells.

The method can be used in order first to oxidise fatty acids or esters thereof and then to aminate them. For this purpose, for example, an enzyme system is suitable, as is described in the international patent application WO 2009/077461. The metabolically active cell in this case is a cell which has a recombinant alkanehydroxylase and a transaminase, preferably, furthermore, at least one enzyme from the group consisting of alcohol dehydrogenase, alanine dehydrogenase and lactam hydrolase.

In the embodiment most preferred, the alkanehydroxylase is an alkanehydroxylase of the AlkB type. AlkB is an oxidoreductase of the AlkBGT system from *Pseudomonas putida*, which is known for the hydroxylase activity thereof. This is dependent on two further polypeptides, AlkG and AlkT, which are preferably co-expressed. AlkT is characterized as an FAD-dependent rubredoxin reductase which transfers the electrons from NADH to AlkG. AlkG is a rubredoxin, an iron-containing redox protein which functions as a direct electron donor for alkB. In a preferred embodiment, the expression "alkanehydroxylase of the alkB type", as used herein, is taken to mean a membrane-sited alkane monooxidase. In a further preferred embodiment, the same expression "alkanehydroxylase of the alkB type" is taken to mean a polypeptide having a sequence homology with increasing preference of at least 75, 80, 85, 90, 92, 94, 96, 98 or 99% to the sequence of the alkB of *Pseudomonas putida* Gpo1 (database code: CAB54050.1). In a further preferred embodiment, the expression is taken to mean a cytochrome-independent monooxygenase. In a further preferred embodiment, the expression "alkanehydroxylase of the alkB type" 5 is taken to mean a cytochrome-independent monooxygenase which uses at least one rubredoxin or homologue as electron donor. In a particularly preferred embodiment, the expression is taken to mean a membrane-sited cytochrome-independent alkanehydroxylase having with increasingly preferably at least 60, 70, 80, 80, 85, 90, 92, 94, 96, 98 or 99% of the sequence of the AlkB of *Pseudomonas putida* Gpo1, which as electron donor requires at least AlkG (CAB54052.1), but preferably the combination of AlkG with the reductase AlkT (CAB54063.1) wherein alkG and/or alkT can also be a homologue of the respective polypeptide. The expression "sequence", as used herein, can relate to the amino acid sequence of a polypeptide and/or to the nucleic acid sequence encoding it. In a further preferred embodiment, an "alkanehydroxylase of the alkB type", as used herein, is a cytochrome-independent oxidoredctase, i.e. an oxidoreductase which does not comprise cytochrome as cofactor. All of the database codes cited in this application are codes of the version available online on Aug. 1, 2012.

In a preferred embodiment, the expression "alcohol dehydrogenase", as used herein, is taken to mean an enzyme which reduces an aldehyde or ketone to the corresponding primary or secondary alcohol, respectively. Examples comprising the alcohol dehydrogenases of *Ralstonia eutropha* (ACB78191.1), *Lactobacillus brevis* (YP_795183.1), *Lactobacillus kefiri* (ACF95832.1), from horse liver, of *Paracoccus pantotrophus* (ACB78182.1) and *Sphingobium yanoikuyae* (EU427523.1) and also the respective variants thereof.

In a preferred embodiment, the expression "transaminase", as used herein, is taken to mean an enzyme which catalyses the transfer of amino groups from a donor molecule, preferably an amino acid, to an acceptor molecule, preferably an α-ketocarboxylic acid. For example, the transaminase of *Chromobacterium violaceum* ATCC 12472 (database code NP_901695) can be used.

In a preferred embodiment, the expression "alanine dehydrogenase", as used herein, is taken to mean an enzyme which catalyses the conversion of L-alanine with consumption of water and $NAD^+$ to pyruvate, ammonia and NADH. For example, the alanine dehydrogenases from *Bacillus subtilis* (database code L20916), *Rhizobium leguminosarum* (database code CP001622), *Vibrio proteolytikus* (database code AF070716), *Mycobacterium tuberculosis* (database code X63069), *Enterobacter aerogenes* (database code AB013821) can be used.

In the most preferred embodiment, the alkanehydroxylase is an alkanehydroxylase of the AlkB type. AlkB is an oxidoreductase from the AlkBGT system from *Pseudomonas putida*, which is known for its hydroxylase activity. This is dependent on two further polypeptides, AlkG and AlkT, which are preferably co-expressed. AlkT is characterized as an FAD-dependent rubredoxin reductase, which transfers electrons from NADH to AlkG. AlkG is a rubredoxin, an iron-containing redox protein which functions as a direct electron donor to AlkB. In a preferred embodiment, the expression "alkanehydroxylase of the alkB type", as used herein, is taken to mean a membrane-sited alkanemonooxidase. In a further preferred embodiment, the same expression "alkanehydroxylase of the AlkB type" is taken to mean a polypeptide having a sequence homology with increasing preference of at least 75, 80, 85, 90, 92, 94, 96, 98 or 99% to the sequence of the AlkB of *Pseudomonas putida* Gpo1 (database code: CAB54050.1). In a further preferred embodiment, the expression is taken to mean a cytochrome-independent monooxygenase. In a further preferred embodiment, the expression "alkanehydroxylase of the alkB type" 5 is taken to mean a cytochrome-independent monooxygenase which uses at least one rubredoxin or homologue as electron donor. In a particularly preferred embodiment, the expression is taken to mean a membrane-sited, cytochrome-independent alkanehydroxylase having with increasing preference at least 60, 70, 80, 80, 85, 90, 92, 94, 96, 98 or 99% of the sequence of the AlkB of *Pseudomonas putida* Gpo1, which requires, as electron donor, at least AlkG (CAB54052.1), but preferably the combination of AlkG with the reductase AlkT (CAB54063.1), wherein alkG and/or alkT can also be a homologue of the respective polypeptide. The expression "sequence" as used herein, can refer to the amino acid sequence of a polypeptide and/or to the nucleic acid sequence encoding this. In a further preferred embodiment, an "alkanehydroxylase of the alkB type", as used herein, is a cytochrome-independent oxidoreductase, i.e. an oxidoreductase which does not comprise cytochrome as cofactor.

In a further preferred embodiment, the alkanehydroxylase is a cytochrome P450-monooxygenase of the CYP153 family. In a preferred embodiment, the expression "cytochrome P450 monooxygenase of the CYP153 family" is taken to mean a cytosolic oxidase which is part of a 3-component system which further comprises a ferredoxin and a ferredoxin reductase, with an alkane binding site and the ability to hydroxylate alkanes. In a particularly preferred embodiment, it is an enzyme which has to at least 80, preferably 90, most preferably 95 or 99%, sequence identity to the cytochrome P450 monooxygenase of the CYP153 family from *Alcanivorax borkumensis* SK2 (database code YP_691921) or an enzyme which comprises a polypeptide sequence which has at least 80, preferably 90, most preferably 95 or 99%, sequence identity to the cytochrome P450 monooxygenase of the CYP153 family from *Alcanivorax borkumensis* SK2 (database code YP_691921) and moreover has alkanehydroxylase activity. In a preferred embodiment, the expression "alkanehydroxylase activity", as used herein, is taken to mean the ability to catalyse the hydroxylation of alkanes or unsubstituted linear alkyl radicals comprising at least five, preferably twelve, carbon atoms. In a further preferred embodiment, the expression "cytochrome P450 monooxygenase of the CYP153 family" is taken to mean a non-membrane-bonded oxidase which includes a binding site for alkanes, unsubstituted linear alkyl radicals comprising at least five, preferably twelve, carbon atoms or monohydroxylated alkanes and the polypeptide chain of which comprises the motif LL(I/L)(V/I)GGNDTTRN. In a preferred embodiment, a "cytochrome P450 monooxygenase of the CYP153 family", as used herein, is a cytochrome P450 monooxygenase of the CYP153 family from *Alcanivorax borkumensis* SK2 (database code YP_691921) or a variant which preferably has alkanehydroxylase activity.

For the optimal supply of the cytochrome P450 monooxygenase of the CYP153 family with electrons from the reducing agent, preferably NADH, it is preferred that the monooxygenase is used together with ferredoxin reductase that interacts functionally with it and ferredoxin that interacts functionally with it. These may be isolated polypeptides or, in the case of using a metabolically active cell, coexpressed polypeptides or polypeptides fused on the N- or C-terminus with the cytochrome P450 monooxygenase of the CYP153 family. Whether a ferredoxin reductase or a ferredoxin with a given cytochrome P450 monooxygenase of the CYP153 family interact functionally with one another can be readily established by a person skilled in the art by whether the reducing agent is oxidized in the presence of an alkane substrate and the three polypeptides. Alternatively, it is possible to use the enzyme test described by Scheps, D., Malca, H., Hoffmann, B., Nestl, B. M, and Hauer, B. (2011) *Org. Biomol. Chem.*, 9, 6727 which, in the case of functionally interacting polypeptides, exhibits a considerable increase in the reaction rate. In a particularly preferred embodiment, the cytochrome P450 monooxygenase of the CYP153 family, the ferredoxin and the ferredoxin reductase originate from the same organism. In a particularly preferred embodiment, it is the ferredoxin reductase from *Alcanivorax borkumensis* SK2 (database code YP_691923) or a variant thereof, the ferredoxin from *Alcanivorax borkumensis* SK2 (database code YP_691920) or a variant thereof and the cytochrome P450 monooxygenase of the CYP153 family from *Alcanivorax borkumensis* SK2 (database code YP_691921) or a variant thereof.

The teaching of the present invention can be not only carried out or applied with use of or on the exact amino acid or nucleic acid sequences of the biological macromolecules described herein, for example via knock-out of a gene which encodes an enzyme catalysing one of the reactions of the β-oxidation, but also with use of or on variants of such macromolecules which can be obtained by deletion, addition or substitution of one or more than one amino acids or nucleic acids. In a preferred embodiment, the expression "variant" of a nucleic acid sequence or amino acid sequence, hereinafter used synonymously and interchangeably with the term "homologue", as used here, means another nucleic acid sequence or amino acid sequence, which has a homology, here used synonymously with identity, of 70, 75, 80, 85, 90, 92, 94, 96, 98, 99% or more percent, with respect to the corresponding original wild-type nucleic acid or amino acid sequence, wherein preferably the amino acids other than the amino acids forming the catalytically active centre or essential for the structure or folding are deleted or substituted or the latter are merely conservatively substituted, for example, a glutamate in place of an aspartate or a leucine in place of a valine. The prior art describes algorithms, which may be used to calculate the degree of homology of two sequences, e.g. Arthur Lesk (2008), Introduction to Bioinformatics, $3^{rd}$ edition. In a further more preferred embodiment of the present invention, the variant of an amino acid or nucleic acid sequence, preferably in addition to the sequence homology mentioned above, has substantially the same enzymatic activity of the wild-type molecule and/or of the original molecule. For example, a variant of an enzymatically active polypeptide protease has the same, or substantially the same, proteolytic activity as the polypeptide enzyme, i.e. the capability to catalyse the hydrolysis of a peptide bond. In a particular embodiment, the expression "substantially the same enzymatic activity" means an activity, with respect to the substrates of the wild-type polypeptide, which clearly lies above the background activity or/and differs from the $K_M$ and/or $k_{cat}$ values by less than 3, more preferably 2, even more preferably one order of magnitude, which the wild-type polypeptide exhibits with respect to the same substrates. In a further preferred embodiment, the expression "variant" of a nucleic acid or amino acid sequence includes at least one active part and/or fragment of the nucleic acid or amino acid sequence. In a further preferred embodiment, the expression "active part", as used here, means an amino acid sequence or a nucleic acid sequence which has less than the full length of the amino acid sequence and/or encodes less than the full length of the amino acid sequence, wherein the amino acid sequence or the encoded amino acid sequence with a shorter length than the wild-type amino acid sequence has substantially the same enzymatic activity as the wild-type polypeptide or a variant thereof, for example, as fatty acid importer, as enoyl-CoA-hydratase or FadE, or as acetyl-CoA-acyltransferase, or FadB. In a particular embodiment, the expression "variant" of a nucleic acid comprises a nucleic acid, the complementary strand of which, preferably under stringent conditions, binds to the wild-type nucleic acid. The stringency of the hybridization reaction is readily determinable by those skilled in the art and depends in general on the length of the probe, the washing temperatures and the salt concentration. Generally, longer probes require higher temperatures for the hybridization, whereas shorter probes work at lower temperatures. Whether hybridization takes place depends in general on the capability of the denatured DNA to anneal to complementary strands which are present in its environment and below the melting temperature. The stringency of hybridization reactions and the corresponding conditions are described in more detail in Ausubel et al. (1995). Instructions for identifying DNA sequences by means of hybridization can be found by the person skilled in the art inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place in a preferred embodiment under stringent conditions, i.e. only hybrids are formed in which probe and target sequence, i.e. the polynucleotides treated with the probe, are at least 70% identical. It is known that the stringency of the hybridization including the washing steps is influenced and/or determined by varying the buffer composition, the temperature and the salt concentration. The hybridization reaction is generally carried out at a relatively lower stringency compared with the washing steps (Hybaid Hybridisation Guide, Hybaid Limited, Teddington, UK, 1996). For the hybridization reaction, for example, a buffer corresponding to 5×SSC buffer can be used at a temperature of about 50° C.-68° C. In this connection, probes can also hybridize with polynucleotides which have less than 70% identity to the sequence of the probe. Such hybrids are less stable and are removed by washing under stringent conditions. This can be achieved for example by lowering the salt concentration to 2×SSC and optionally subsequently 0.5× SSC (The DIG System User's Guide for Filter Hybridisation, Boehringer Mannheim, Mannheim, Germany, 1995), in which case a temperature of, increasing in order of preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. is established. Temperature ranges from about 64° C.-68° C. or about 66° C.-68° C. are preferred. It is optionally possible to reduce the salt concentration down to a concentration corresponding to 0.2×SSC or 0.1×SSC. By means of a stepwise increase in the hybridization temperature in steps of about 1-2° C. from 50° C. to 68° C., polynucleotide fragments can be isolated which, for example in the order of increasing preference, have at least 70% or at least 80% or at least 90%, at least 91%, at least 92%, at least 93%, at least 94%, at least 95%, at least 96%, at least 97%, at least 98% or at least 99% identity to the sequence of the nucleic acid molecule used. Further instructions relating to the hybridization are commercially available in the form of so-called kits (e.g. DIG Easy Hyb from Roche Diagnostics GmbH, Mannheim, Germany, Catalogue No. 1603558). In a preferred embodiment, the expression "variant" of a nucleic acid, as used here, comprises any nucleic acid sequence which encodes the same amino acid sequence as the original nucleic acid or a variant of this amino acid sequence in the context of the degeneracy of the genetic code.

After the second step, the hydrophobic organic solution is separated off from the aqueous culture medium. Owing to the inherent capacity of this system for developing two phases, this is an operation which is easy to carry out for a person skilled in the art, who can proceed simply by allowing the vessel to stand and subsequently decanting off one phase. Alternatively, a separating funnel can be used. If the boiling points differ sufficiently, there is the possibility, by applying reduced pressure, of taking off the lower-boiling phase, which is generally the organic phase. Small amounts of water remaining in the organic phase can be removed by using inorganic desiccants such as calcium hydride, anhydrous calcium chloride, silica gel, anhydrous sodium sulphate, sodium hydroxide or the like.

Further instructions for carrying out the invention can be found in PCT/EP2011/071491, wherein the fatty acids described there need to be replaced by those according to the invention.

The invention claimed is:

1. A reaction mixture, comprising
an aqueous solution comprising an organic compound, and
a hydrophobic organic solution comprising a liquid hydrophobic cation exchanger,
wherein
the liquid hydrophobic cation exchanger is a saturated alkanoic acid comprising an alkyl substituent which has at least 12 carbon atoms, and
the organic compound is a compound of formula (II)

$$NR^2R^3H^+\text{-}A\text{-}NR^4R^5H^+ \qquad (II),$$

wherein
A is an alkylene group comprising at least three carbon atoms, and
$R^2$, $R^3$, $R^4$, and $R^5$, each independently, are selected from the group consisting of methyl, ethyl, propyl and butyl.

2. The reaction mixture according to claim 1, wherein the liquid hydrophobic cation exchanger is a branched-chain fatty acid of formula $(H_3C)_2CH\text{---}(CH_2)_n\text{---}COOH$, or an unprotonated form thereof, and n is at least 4.

3. The reaction mixture according to claim 1, wherein the liquid cation exchanger is a branched-chain fatty acid which comprises substituents that are other than cyclic substituents.

4. The reaction mixture according to claim 1, wherein the aqueous solution further comprises a metabolically active cell.

5. The reaction mixture according to claim 1, wherein the organic compound is a diamine selected from the group consisting of 1,4-butanediamine, 1,5-pentanediamine, 1,6-hexanediamine, 1,8-octanediamine, 1,14-tetradecanediamine, 1,18-octadecanediamine, 2-methyl-1,5-diaminopentane, 2,2 dimethyl-1,5-diaminopentane, 4,4'-diaminodicyclohexylmethane, 3,3'-dimethyl-4,4'-diaminodicyclohexylmethane, 3,3',5,5'-tetramethyl-4,4'-diaminodicyclohexylmethane, 2,2,4- or 2,4,4-trimethylhexamethylenediamine, 1,4-diaminocyclohexane, 4,4'-diaminodicyclohexylpropane, and isophoronediamine.

6. The reaction mixture according to claim 1, wherein a molar ratio of the liquid cation exchanger to the organic compound is at least 1.

7. The reaction mixture according to claim 1, wherein a molar ratio of the liquid cation exchanger to the organic compound is from 1.5 to 3.

8. The reaction mixture according to claim 1, wherein a volumetric ratio of the hydrophobic organic solution to the aqueous solution is 100:1 to 1:100.

9. The reaction mixture according to claim 1, wherein a volumetric ratio of the hydrophobic organic solution to the aqueous solution is 20:1 to 1:20.

10. The reaction mixture according to claim 1, wherein a volumetric ratio of the hydrophobic organic solution to the aqueous solution is 2:1 to 1:2.

* * * * *